US009883802B2

(12) United States Patent
 Ito

(10) Patent No.: US 9,883,802 B2
(45) Date of Patent: Feb. 6, 2018

(54) MEASUREMENT PROBE

(71) Applicant: OLYMPUS CORPORATION, Tokyo (JP)

(72) Inventor: Ryosuke Ito, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 651 days.

(21) Appl. No.: 14/478,660

(22) Filed: Sep. 5, 2014

(65) Prior Publication Data

US 2014/0378847 A1    Dec. 25, 2014

Related U.S. Application Data

(63) Continuation of application No. PCT/JP2013/056185, filed on Mar. 6, 2013.
(Continued)

(51) Int. Cl.
*A61B 5/00* (2006.01)
*A61B 1/00* (2006.01)
*A61B 1/015* (2006.01)

(52) U.S. Cl.
CPC ........ *A61B 5/0059* (2013.01); *A61B 1/00165* (2013.01); *A61B 1/015* (2013.01);
(Continued)

(58) Field of Classification Search
CPC .... A61B 5/0059; A61B 1/00165; A61B 1/015
See application file for complete search history.

(56) References Cited

U.S. PATENT DOCUMENTS

2003/0232445 A1   12/2003   Fulghum, Jr.
2007/0129615 A1    6/2007   Backman et al.
(Continued)

FOREIGN PATENT DOCUMENTS

JP    A-2002-535645    10/2002
JP    A-2005-515473     5/2005
(Continued)

OTHER PUBLICATIONS

Kim et al., "Low-coherence Enhanced Backscattering: Review of Principles and Applications for Colon Cancer Screening," *Journal of Biomedical Optics*, 2006, vol. 11 No. 4, pp. 041125-1 to 041125-10.
(Continued)

*Primary Examiner* — Joseph Dietrich
(74) *Attorney, Agent, or Firm* — Oliff PLC

(57) ABSTRACT

A measurement probe is configured to be detachably connected to an optical measurement apparatus for optically measuring a living tissue and includes: an illuminating fiber configured to apply illumination light to the living tissue; a plurality of light receiving fibers configured to receive, at different positions, the backscattering light which is applied by the illuminating fiber and backreflected and/or backscattered from the living tissue; and a support section that is substantially cylindrical and configured to make a distance from each distal end of the illuminating fiber and the plurality of light receiving fibers to the living tissue constant, and permit the illumination light to pass through at least a part of a side surface thereof. An illumination area of the illumination light applied by the illuminating fiber on the living tissue is larger than the area of a distal end of the support section.

13 Claims, 11 Drawing Sheets

Related U.S. Application Data

(60) Provisional application No. 61/607,715, filed on Mar. 7, 2012.

(52) U.S. Cl.
CPC .......... *A61B 5/0075* (2013.01); *A61B 5/0084* (2013.01); *A61B 2562/0233* (2013.01); *F04C 2270/0421* (2013.01)

(56) References Cited

U.S. PATENT DOCUMENTS

2009/0009759 A1   1/2009   Backman et al.
2010/0262020 A1   10/2010  Backman et al.

FOREIGN PATENT DOCUMENTS

| JP | 3803166 B2 | 8/2006 |
| JP | A-2009-537285 | 10/2009 |
| WO | WO 00/43750 | 7/2000 |
| WO | WO 2010/081048 A1 | 7/2010 |

OTHER PUBLICATIONS

Turzhitsky et al., "Characterization of Light Transport in Scattering Media at Subdiffusion Length Scales with Low-Coherence Enhanced Backscattering," *IEEE Journal of Selected Topics in Quantum Electronics*, 2010, vol. 16 No. 3, pp. 619-626.

Roy et al., "Association Between Rectal Optical Signatures and Colonic Neoplasia: Potential Applications for Screening," *Cancer Research*, 2009, vol. 69 No. 10, pp. 4476-4483.

International Search Report issued in PCT/JP2013/056185 dated Apr. 16, 2013.

Mar. 20, 2015 Extended Supplementary European Search Report issued in European Application No. 13 75 7769.8.

MEASUREMENT PROBE

CROSS-REFERENCE TO RELATED APPLICATIONS

This application is a continuation of PCT international application No. PCT/JP2013/056185 filed on Mar. 6, 2013 which designates the United States, incorporated herein by reference, and which claims the benefit of priority from U.S. provisional application No. 61/607,715, filed on Mar. 7, 2012, incorporated herein by reference.

BACKGROUND OF THE INVENTION

1. Field of the Invention

The present invention relates to a measurement probe to be connected to an optical measurement apparatus that applies measurement light to a living tissue, and estimates the properties of the living tissue based on a measurement value of the measurement light reflected and/or scattered back from the living tissue.

2. Description of the Related Art

Backscattered light in the backward direction from a relatively weak scattering medium such as a living tissue is conventionally known to be observed as enhanced backscattering light according to the degree of spatial coherence (spatial coherence) of the illumination light (see Young L. Kim, et. al, "Low-coherence enhanced backscattering; review of principles and applications for colon cancer screening" Journal of Biomedical Optics, 11(4), 041125 Year 2006). A spectral information measurement technique using this phenomenon is called LEBS (Low-coherence Enhanced Backscattering Spectroscopy), and the relationship between angular pattern of enhanced backscattering and the optical properties of the scattering medium are studied well (see V, Turzhitsky, et. al, "Characterization of Light transport in Scattering Media at Subdiffusion Length Scales with Low-Coherence Enhanced Backscattering" IEEE journal of selected topics in quantum electronics, Vol. 16, No. 3, 619 (2010)). The scattering mean free path (the inverse of the scattering coefficient) is correlated with a change in the internal structure of the scattering medium and is used to detect minute changes in the tissue structure such as those observed in cancer in the early stage. For example, it is known that the use of the profile of enhanced backscattering light enables the identification of colorectal cancer (see Hemant K. Roy, et. al, "Association between Rectal Optical Signatures and Colonic Neoplasia: Potential Applications for Screening" Cancer Research, 69(10), 4476 (2009)).

In the above-mentioned LEBS, a technique is known which applies LEBS to non-invasive measurement in the body through a measurement probe inserted in an endoscope (See U.S. Patent Publication No. 2009/0009759). In this technique, in order to acquire an enhanced backscattering light, illumination light is applied to a living tissue from a distal end of an illuminating fiber of the measurement probe. A plurality of light receiving fibers is used to measure the intensity distribution of scattered light at a plurality of scattering angles. Accordingly, the properties of the living tissue are detected.

SUMMARY OF THE INVENTION

A measurement probe according to one aspect of the present invention is configured to be detachably connected to an optical measurement apparatus for optically measuring a living tissue. The measurement probe includes: an illuminating fiber configured to apply illumination light to the living tissue; a plurality of light receiving fibers configured to receive, at different positions, the backscattering light which is applied by the illuminating fiber and backreflected and/or backscattered from the living tissue; and a support section that is substantially cylindrical and configured to make a distance from each distal end of the illuminating fiber and the plurality of light receiving fibers to the living tissue constant, and permit the illumination light to pass through at least a part of a side surface thereof. An illumination area of the illumination light applied by the illuminating fiber on the living tissue is larger than the area of a distal end of the support section.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
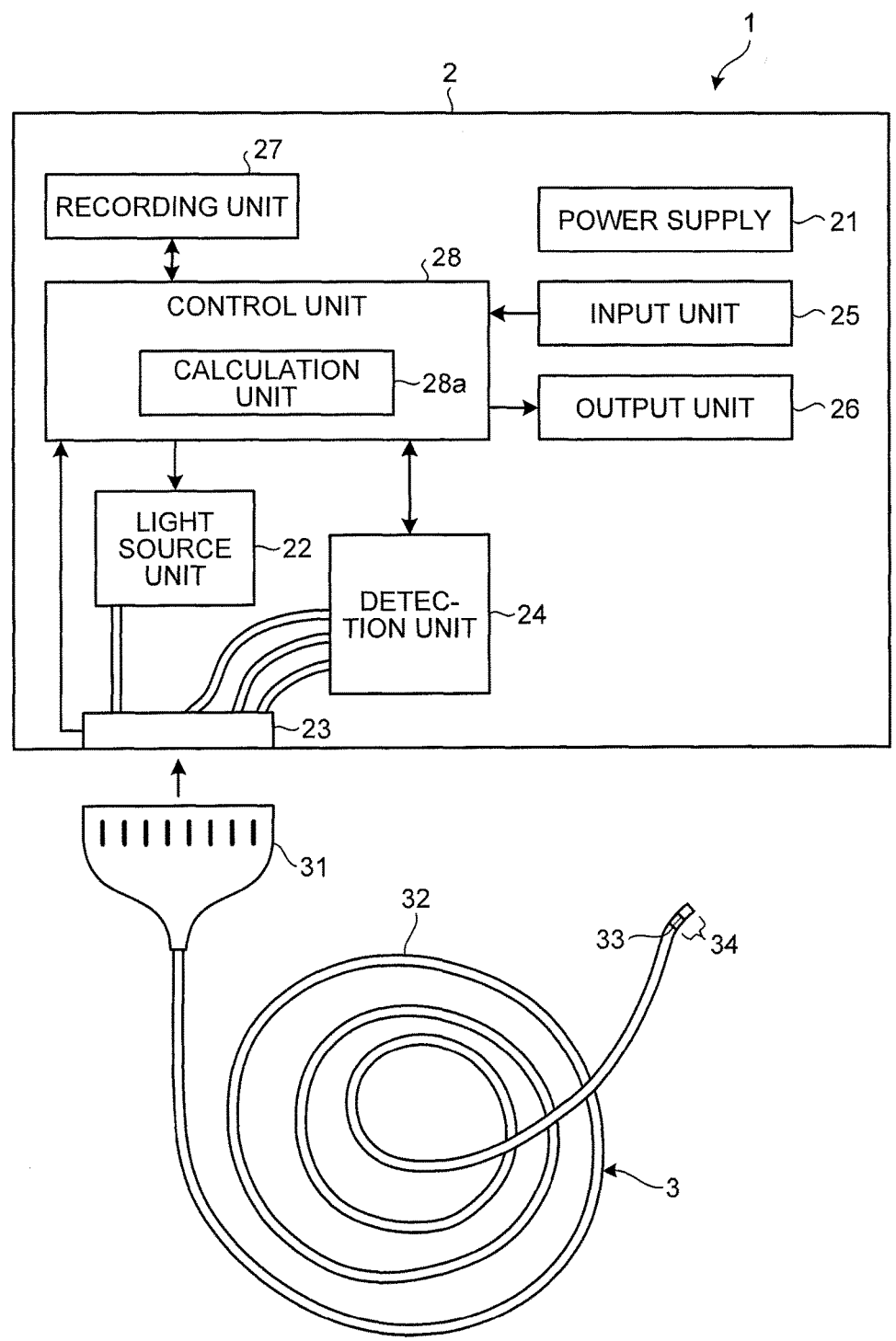
FIG. 1 is a block diagram schematically illustrating a configuration of an optical measurement apparatus according to a first embodiment of the present invention.

Hereinafter, preferred embodiments of an optical measurement apparatus and an endoscope system according to the present invention are described in detail, taking an optical measurement apparatus using the LEGS technique as an example, with reference to the drawings. Moreover, the present invention is not limited by the embodiments. Moreover, a description is given in the description of the drawings, assigning the same reference numerals to the same parts. Moreover, the drawings are schematic, and it should be noted that the relationship between the thickness and width of each member, the ratio of the members, and the like are different from actual ones. Moreover, parts whose dimensions and ratios are different among the drawings are also included.

First Embodiment

FIG. 1 is a block diagram schematically illustrating a configuration of an optical measurement apparatus according to a first embodiment of the present invention. An optical measurement apparatus 1 illustrated in FIG. 1 includes a main body unit 2 that optically measures a measurement target object such as a living tissue and measures the optical characteristics of the measurement target object, and a measurement probe 3 that is detachably connected to the main body unit 2 and is inserted into a subject via a treatment instrument channel of an endoscope.

Firstly, the main body unit 2 is described. The main body unit 2 includes a power supply 21, a light source unit 22, a connection unit 23, a detection unit 24, an input unit 25, an output unit 26, a recording unit 27, and a control unit 28. The power supply 21 supplies electric power to each component of the main body unit 2.

The light source unit 22 emits light having at least one spectral component to apply to the measurement target object via the connection unit 23, to the measurement probe 3 as illumination light. The light source unit 22 is constructed using a light source such as an LED (Light Emitting Diode), a xenon lamp, a tungsten lamp, a halogen lamp, or a laser, an optical system including a plurality of lenses such as condenser lenses or collimator lenses, a light source driver, and the like. The light source unit 22 emits the illumination light toward the measurement probe 3 under the control of the control unit 28. For example, the light source unit 22 switches between turning-on and -off of the illumination light under the control of the control unit 28. The light source unit 22 concentrates the light emitted from the light source onto the measurement probe 3 by the optical system. Accordingly, the beam combining efficiency between the light source and the measurement probe increases, and hence the amount of the illumination light increases. Accordingly, the measurement quality of a measurement target object S1 can be improved.

The connection unit 23 connects a proximal end section 31 (a connector section) of the measurement probe 3 detachably to the main body unit 2. The connection unit 23 propagates, to the measurement probe 3, the illumination light emitted by the light source unit 22, and propagates, to the detection unit 24, the backscattering light which is applied by the illuminating fiber and backreflected and/or backscattered from the living tissue via the measurement probe 3.

The detection unit 24 detects the backscattering light which is applied by the illuminating fiber and backreflected and/or backscattered from the living tissue via the measurement probe 3. The detection unit 24 is constructed using, for example, a plurality of spectral elements and/or light receiving sensors such as CCDs (Charge Coupled Device), CMOSs (Complementary Metal Oxide Semiconductor), or PDs (Photo Detector). Specifically, the detection unit 24 is provided with spectrophotometers in agreement in number with the light receiving fibers of the measurement probe 3, which is described below. Moreover, the detection unit 24 measures the spectrum and/or intensity distribution of scattered light incident from the measurement probe 3, detects the intensity according to the wavelength, and outputs the detection results to the control unit 28.

The input unit 25 accepts the input of an instruction signal that instructs the start of the main body unit 2 or other instruction signals that instruct various operations, and outputs the instruction signal to the control unit 28. The input unit 25 is constructed using input devices such as a push switch, a touchscreen, a keyboard, and a mouse.

The output unit 26 outputs information on various processes in the optical measurement apparatus 1, and measurement results of the measurement target object. The output unit 26 is constructed using a display such as a liquid crystal display or an organic EL (Electro Luminescence) display, a speaker, and the like.

Various programs for operating the optical measurement apparatus 1 and various data and parameters to be used for an optical measurement process are recorded in the recording unit 27. Information in process by the optical measurement apparatus 1 is temporarily recorded in the recording unit 27. Moreover, the measurement results of the measurement target object are recorded in the recording unit 27. The recording unit 27 is constructed using a volatile memory, non-volatile memory, or the like. The recording unit 27 may be constructed using a memory card to be attached from the outside of the main body unit 2, or the like.

The control unit 28 controls the processing operation of each unit of the main body unit 2. The control unit 28 centrally controls the operation of the main body unit 2 by, for example, transferring instruction information and data to each unit of the main body unit 2. The control unit 28 is constructed using a CPU (Central Processing Unit) and the like. Moreover, the control unit 28 includes a calculation unit 28a.

The calculation unit 28a performs a plurality of calculation processes based on the detection results detected by the detection unit 24 and calculates the characteristic values related to the optical characteristics and properties of the measurement target object. The type of the characteristic values is set in accordance with, for example, the instruction signal accepted by the input unit 25, or various programs recorded in the recording unit 27.

Next, the measurement probe 3 is described. The measurement probe 3 is constructed such that a plurality of optical fibers is arranged inside. Specifically, the measurement probe 3 is constructed using an illuminating fiber that applies the illumination light to the measurement target object, a plurality of light receiving fibers that receive, at different scattering angles, the backscattering light which is applied by the illuminating fiber and backreflected and/or backscattered from the living tissue, and a support section that keeps a constant distance between a distal end of each of the illuminating fiber and the plurality of light receiving fibers and the target object. The measurement probe 3 includes a proximal end section 31 (a connector) to be connected to the connection unit 23 of the main body unit 2, a flexible section 32 having flexibility, a distal end portion 33 that applies the illumination light supplied from the light source unit 22, and receives the light returned from the measurement target object, and a support section 34 that is detachable from the distal end portion 33, and keeps the distance from the measurement target object constant.

Figure 2:
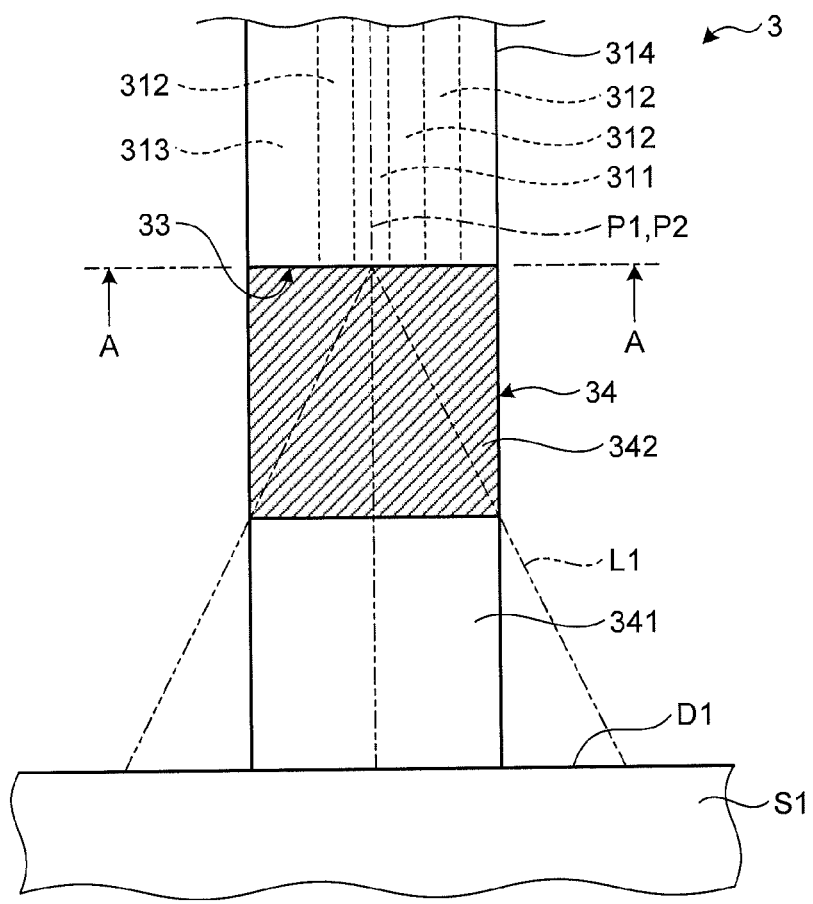
FIG. 2 is a side view schematically illustrating a configuration of a distal end portion of a measurement probe including a support section according to the first embodiment of the present invention.
Figure 3:
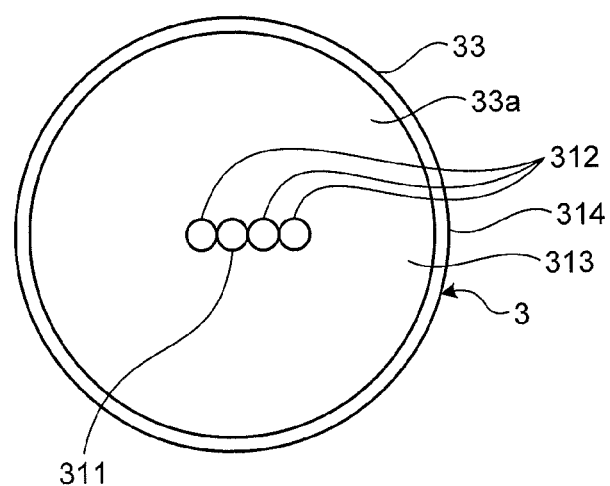
FIG. 3 is a cross-sectional view taken along line A-A of FIG. 2.
Figure 4:
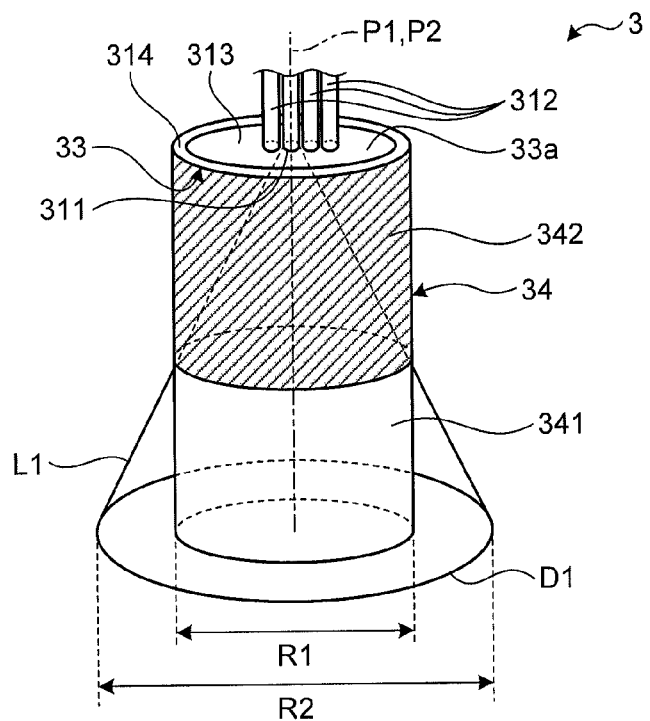
FIG. 4 is a perspective view schematically illustrating a configuration of the distal end portion of the measurement probe including the support section according to the first embodiment of the present invention.

A detailed description is given of the configuration of the distal end portion 33 of the measurement probe 3 including the support section 34. FIG. 2 is a side view schematically illustrating the configuration of the distal end portion 33 of the measurement probe 3 including the support section 34. FIG. 3 is a cross-sectional diagram taken along line A-A of FIG. 2, and is a diagram illustrating an end surface 33a of the distal end portion 33 of the measurement probe 3. FIG. 4 is a perspective view schematically illustrating the configuration of the distal end portion 33 of the measurement probe 3 including the support section 34.

As illustrated in FIGS. 2 to 4, the measurement probe 3 includes an illuminating fiber 311 that applies the illumination light to the measurement target object S1, three light receiving fibers 312 that receive the backscattering light which is applied by the illuminating fiber 311 and backreflected and/or backscattered from the measurement target object S1, a holding section 313 that holds the illuminating fiber 311 and the three light receiving fibers 312, a coated section 314 made of resin or the like to prevent damage to and fix the positions of the illuminating fiber 311, the light receiving fibers 312, and the holding section 313, and the support section 34 that keeps a constant distance between end surfaces of the distal ends of the illuminating fiber 311 and the light receiving fibers 312, and the measurement target object S1. In the measurement probe 3, the illuminating fiber 311 and the three light receiving fibers 312 are arranged at the end surface 33a of the distal end portion 33 in a state where of neighboring one another in a straight line.

The illuminating fiber 311 is constructed using an optical fiber. The illuminating fiber 311 propagates the illumination light emitted from the light source unit 22, and applies the illumination light to the measurement target object from the end surface 33a of the distal end portion 33 via the support section 34. A central axis P2 of luminous flux L1 of the illumination light applied by the illuminating fiber 311 agrees with a central axis P1 of the measurement probe 3.

The light receiving fiber 312 is constructed using an optical fiber. The light receiving fibers 312 receive, at different positions which correspond to different scattering angles, the backscattering light which is applied by the illuminating fiber and backreflected and/or backscattered from the measurement target object to the detection unit 24. The number of the light receiving fibers 312 can be changed as appropriate according to the examination item or the kind of measurement target object, for example, the blood flow or site. At least two or more light receiving fibers are required.

The holding section 313 holds the illuminating fiber 311 and the light receiving fibers 312. The holding section 313 holds the distal ends of the illuminating fiber 311 and the three light receiving fibers 312 at the end surface 33a of the distal end portion 33 in the state where the distal ends neighbor one another in a straight line. The holding section 313 is constructed using glass material, resin, brass, or the like. Furthermore, the holding section 313 holds the illuminating fiber 311 and the light receiving fibers 312 while causing the central axis P2 of the illuminating fiber 311 to agree with the central axis of the measurement probe 3.

The coated section 314 protects the illuminating fiber 311, the light receiving fibers 312, and the holding section 313 from the external force. The coated section 314 is constructed using resin or the like.

The support section 34 is provided to the distal end portion 33 of the measurement probe 3, keeps a constant distance between the distal ends of the illuminating fiber 311 and the three light receiving fibers 312 and the measurement target object S1, and has a cylindrical shape that at least a part of its side surface permits the passage of the illumination light applied by the illuminating fiber 311. The support section 34 includes an optical member 341 having a predetermined refractive index, and a reinforcement member 342 that protects the optical member 341.

The optical member 341 has a cylindrical shape and relays the illumination light emitted by the illuminating fiber 311 and applies the illumination light to the measurement target object S1. The optical member 341 is constructed using transmissive glass material, plastic or the like that has a predetermined refractive index, and transmits the luminous flux L1 of the illumination light applied by the illuminating fiber 311. Furthermore, the optical member 341 flattens the surface of the measurement target object S1 with an end surface of the optical member 341. Consequently, the optical measurement apparatus 1 can measure the measurement target object S1 without being influenced by the unevenness of the surface of the measurement target object S1.

The reinforcement member 342 is in contact with a side wall of the optical member 341, and forms at least a part of its side surface to be smaller than the length of the optical member 341 in the longitudinal direction, using a material that absorbs the illumination light applied by the illuminating fiber 311. For example, the reinforcement member 342 is formed using a material that is resistant to reflections, such as metal or resin. The reinforcement member 342 prevents the optical member 341 from being bent or damaged by relieving the external force on the optical member 341. The optical member 341 and the reinforcement member 342 may be integrally formed.

The measurement probe 3 constructed in this manner is formed such that an illumination area D1 (a diameter R2 of the illumination area D1) on the measurement target object S1 to which the illuminating fiber 311 applies light is larger than the area of the distal end of the support section 34 (an outer diameter R1 of the support section 34). In this case, a part of the luminous flux L1 of the illumination light applied from the illuminating fiber 311 passes through the side surface of the support section 34. The reinforcement member 342 is formed in such a manner as to cover the side surface of the optical member 341, the side surface not transmitting the luminous flux L1 of the illumination light. Specifically, if the reinforcement member 342 covers the side surface of the optical member 341, it is desired that an area that is shielded (masked) from the luminous flux L1 of the illumination light be 50% or less compared with an area that is not shielded. For example, the side surface of the reinforcement member 342 is formed to have an area with approximately half the length of the optical member 341 in the longitudinal direction.

According to the above-described first embodiment of the present invention, it is possible to acquire a larger amount of information from the measurement target object S1 while promoting a reduction in the diameter of the probe 3. Accordingly, measurements can be made with higher accuracy.

Furthermore, according to the first embodiment of the present invention, the illumination light applied by the illuminating fiber 311 passes (is transmitted) through the side surface of the support section 34. Accordingly, the diameter of the measurement probe can be reduced while stray light (noise) to be detected by the light receiving fibers 312 is suppressed.

Moreover, according to the first embodiment of the present invention, the reinforcement member 342 is provided on the proximal end side of the side surface of the optical member 341. Accordingly, it is possible to prevent the support section 34 from being damaged or dropping off due to the external force.

In the first embodiment of the present invention, a light-shielding member in black or the like, instead of the reinforcement member 342, may be provided on the proximal end side of the optical member 341 to form an untransmissive portion that absorbs light on the side surface of the optical member 341.

Moreover, in the first embodiment of the present invention, a distal end of a distal end portion of the optical member 341 may be inclined with respect to the longitudinal direction (the central axis P1 of the measurement probe 3).

First Modification of First Embodiment

Figure 5:
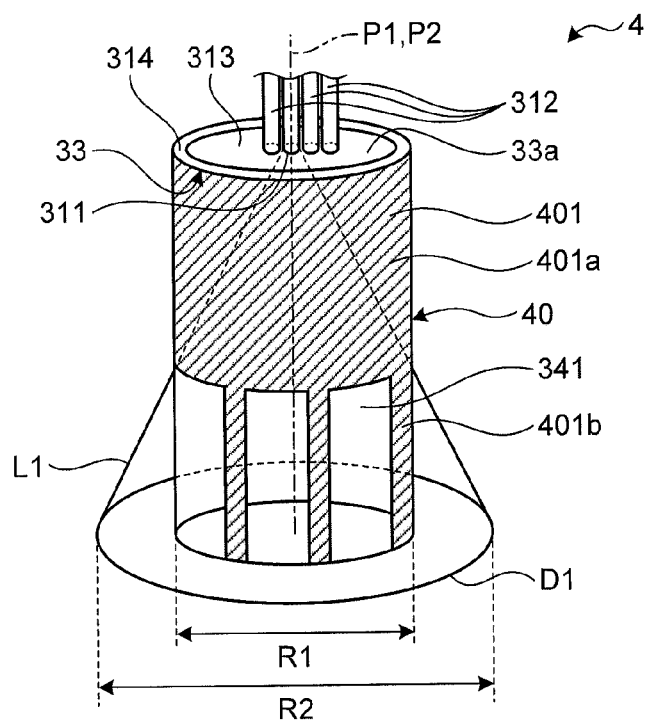
FIG. 5 is a perspective view schematically illustrating a distal end portion of a measurement probe including a support section according to a first modification of the first embodiment of the present invention.

In the first embodiment of the present invention, it is also possible to change the shape of the support section. FIG. 5 is a perspective view schematically illustrating a distal end portion of a measurement probe including a support section according to a first modification of the first embodiment of the present invention. The same reference numerals are assigned to parts having the same configurations as those of the optical measurement apparatus according to the above-mentioned first embodiment, and their descriptions are omitted.

As illustrated in FIG. 5, a measurement probe 4 includes the illuminating fiber 311, the light receiving fibers 312, the holding section 313, the coated section 314, and a support section 40 that keeps a constant distance between end surfaces of the distal ends of the illuminating fiber 311 and the light receiving fibers 312, and the measurement target object S1.

The support section 40 includes the optical member 341, and a reinforcement member 401 that reinforces the optical member 341.

The reinforcement member 401 prevents the optical member 341 from being bent or damaged by the application of the external force to the optical member 341. The reinforcement member 401 includes a tubular tube portion 401a, and a plurality of side portions 401b provided at predetermined intervals extending from the edge of the tube portion 401a toward the distal end. The tube portion 401a and the side portions 401b are integrally formed. The tube portion 401a and the side portions 401b are formed using a material that is resistant to reflections, such as metal or resin.

The measurement probe 4 constructed in this manner is formed such that the diameter R2 of the illumination area D1 on the measurement target object S1 to which the illuminating fiber 311 applies light is larger than the outer diameter R1 of the measurement probe 4 (see FIG. 5). In this case, a part of the luminous flux L1 of the illumination light applied from the illuminating fiber 311 passes through a side surface of the support section 40. At this point in time, it is desired for the reinforcement member 401 that an area that is shielded from the luminous flux L1 of the illumination light be 50% or less compared with when being not shielded at all.

According to the above-described first modification of the first embodiment of the present invention, it is possible to keep stray light incident from the outside to a minimum and further enhance the strength of the distal end portion of the measurement probe 4 while promoting a reduction in the diameter.

Second Modification of First Embodiment

Figure 6:
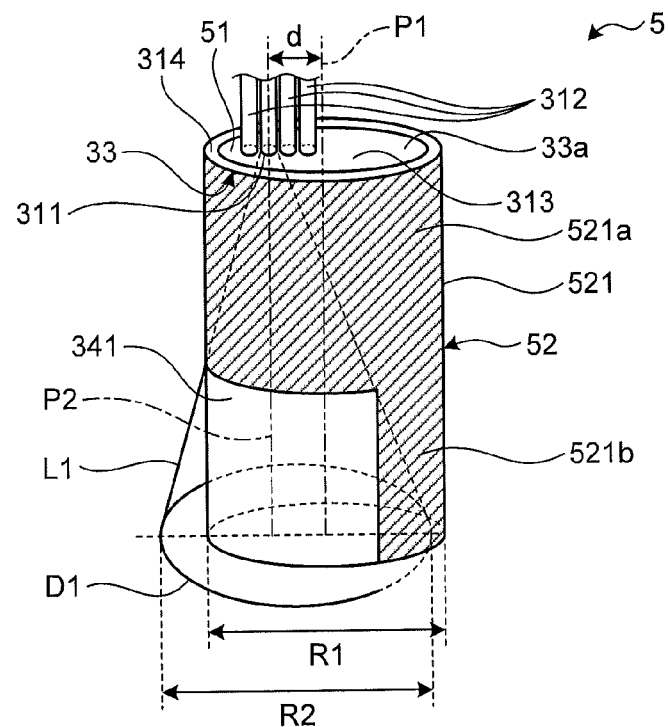
FIG. 6 is a perspective view schematically illustrating a distal end portion of a measurement probe including a support section according to a second modification of the first embodiment of the present invention.

FIG. 6 is a perspective view schematically illustrating a distal end portion of a measurement probe including a support section according to a second modification of the first embodiment of the present invention.

As illustrated in FIG. 6, a measurement probe 5 includes the illuminating fiber 311, the light receiving fibers 312, a holding section 51, the coated section 314, and a support section 52. Included is the support section 52 that keeps a constant distance between the end surfaces of the distal ends of the illuminating fiber 311 and the light receiving fibers 312 and the measurement target object S1.

The holding section 51 holds the distal ends of the illuminating fiber 311 and the three light receiving fibers 312 at the end surface 33a of the distal end portion 33 in the state where the distal ends are arranged in a straight line. Moreover, the holding section 51 holds the illuminating fiber 311 such that the central axis P2 of the luminous flux L1 of the illumination light applied by the illuminating fiber 311 agrees with a position a predetermined distance d away from the central axis P1 of the measurement probe 5. Furthermore, the holding section 51 holds the illuminating fiber 311 such that the central axis P1 of the measurement probe 5 is parallel to the central axis P2 of the luminous flux L1 of the illumination light applied by the illuminating fiber 311 in the same plane. Consequently, the illumination area D1 on the measurement target object S1 to which the illuminating fiber 311 applies light is formed at an off-center position from the central axis P1 of the measurement probe 5, and the diameter R2 of the illumination area D1 on the measurement target object S1 is formed larger than the outer diameter R1 of the measurement probe 5.

The support section 52 keeps a constant distance between the end surfaces of the distal ends of the illuminating fiber 311 and the light receiving fiber 312 and the measurement target object S1. The support section 52 includes the optical member 341, and a reinforcement member 521 that reinforces the optical member 341.

The reinforcement member 521 prevents the optical member 341 from being bent or damaged on the surface by the application of the external force to the optical member 341. The reinforcement member 521 includes a tubular tube portion 521a, and a side portion 521b provided with an arc-shaped cross section, the side portion 521b extending from the edge of the tube portion 521a toward the distal end. The tube portion 521a and the side portion 521b are integrally formed. The tube portion 521a and the side portion 521b are formed using a material that is resistant to reflections, such as metal or resin. The reinforcement member 521 is formed such that an area that is shielded from the luminous flux L1 of the illumination light applied by the illuminating fiber 311 is 50% or less compared with an area that is not shielded at all.

According to the above-described second modification of the first embodiment of the present invention, it is possible to keep stray light incident from the outside to a minimum and further enhance the strength of the distal end portion 33 of the measurement probe 5 while promoting a reduction in the diameter.

Third Modification of First Embodiment

Figure 7:
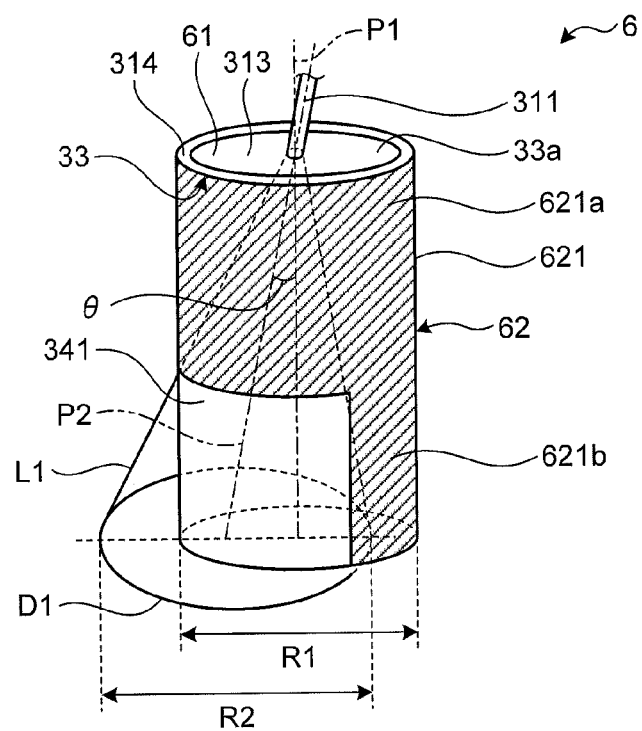
FIG. 7 is a perspective view schematically illustrating a distal end portion of a measurement probe including a support section according to a third modification of the first embodiment of the present invention.

FIG. 7 is a perspective view schematically illustrating a distal end portion of a measurement probe including a support section according to a third modification of the first embodiment of the present invention.

As illustrated in FIG. 7, a measurement probe 6 includes the illuminating fiber 311, the light receiving fibers 312, a holding section 61, the coated section 314, and a support section 62.

The holding section 61 holds the distal ends of the illuminating fiber 311 and the three light receiving fibers 312 such that the distal ends are arranged in a straight line. Moreover, the holding section 61 holds the illuminating fiber 311 at a tilt such that an angle that the central axis P2 of the luminous flux L1 of the illumination applied by the illuminating fiber 311 forms with the central axis P1 of the measurement probe 6 is a predetermined angle θ. Consequently, the illumination area D1 on the measurement target object S1 to which the illuminating fiber 311 applies light is formed at an off-center position from the central axis P1 of the measurement probe 6, and the diameter R2 of the illumination area D1 on the measurement target object S1 is formed larger than the outer diameter R1 of the measurement probe 6.

The support section 62 includes the optical member 341, and a reinforcement member 621 that reinforces the optical member 341.

The reinforcement member 621 prevents the optical member 341 from being bent or damaged on the surface by the application of the external force to the optical member 341. The reinforcement member 621 includes a tubular tube portion 621a, and a side portion 621b provided with an arc-shaped cross section, the side portion 621b extending from the edge of the tube portion 621a toward the distal end. The tube portion 621a and the side portion 621b are integrally formed. The tube portion 621a and the side portion 621b are formed using a material that is resistant to reflections, such as metal or resin. In the reinforcement member 621 constructed in this manner, an area that is shielded from the luminous flux L1 of the illumination light applied by the illuminating fiber 311 is formed larger than an area that transmits the luminous flux L1 of the illumination light.

According to the above-described third modification of the first embodiment of the present invention, it is possible to keep stray light incident from the outside to a minimum and further enhance the strength of the support section 62 while promoting a reduction in the diameter.

Second Embodiment

Next, a second embodiment of the present invention is described. A measurement probe according to the second embodiment is hollow inside, instead of the optical member of the support section. Hence, a description is given below of a configuration of the measurement probe according to the second embodiment. The same reference numerals are assigned to the same configurations as those of the optical measurement apparatus according to the above-mentioned first embodiment and their descriptions are omitted.

Figure 8:
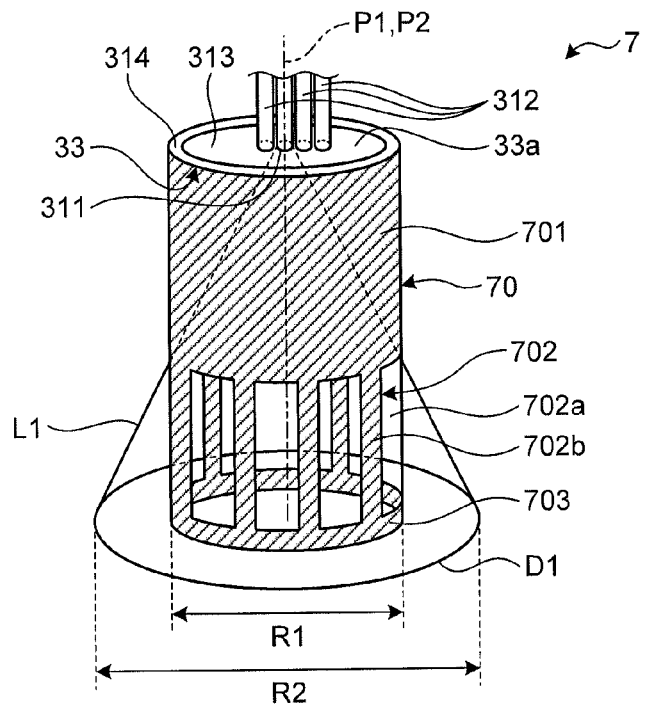
FIG. 8 is a perspective view schematically illustrating a distal end portion of a measurement probe including a support section according to a second embodiment of the present invention.

FIG. 8 is a perspective view schematically illustrating a distal end portion of a measurement probe including a support section according to the second embodiment of the present invention.

A measurement probe 7 illustrated in FIG. 8 includes the illuminating fiber 311, the light receiving fibers 312, the holding section 313, the coated section 314, and a support section 70.

The support section 70 is provided to the end surface 33a of the distal end portion 33 of the measurement probe 7. The support section 70 has the same diameter as the outer diameter of the measurement probe 7, is formed of a member that absorbs the illumination light, and includes a substantially cylindrical tube portion 701 having a hollow tubular shape, an illumination restriction portion 702 provided at a distal end of the tube portion 701 with window portions 702a that permit at least part of the illumination light applied by the illuminating fiber 311 to pass through, the illumination restriction portion 702 being formed of a member that absorbs the illumination light, and an annular-shaped annular portion 703 provided at a distal end of the illumination restriction portion 702. The tube portion 701, the illumination restriction portion 702, and the annular portion 703 are integrally formed. Moreover, the tube portion 701, the illumination restriction portion 702, and the annular portion 703 are formed of a material that is resistant to reflections, such as metal or resin. The window portions 702a are formed in the illumination restriction portion 702 by side portions 702b formed along the edge of the tube portion 701 at predetermined intervals. Consequently, the side portions 702b do not have a refracting surface, and hence it is possible to prevent the influence of irregular reflection of the illumination light reflected from the side portions 702b.

In the measurement probe 7 constructed in this manner, the diameter R2 of the illumination area D1 on the measurement target object S1 to which the illuminating fiber 311 applies light is formed larger than the outer diameter R1 of the measurement probe 7. In this case, a part of the luminous flux L1 of the illumination light applied from the illuminating fiber 311 passes through the side surface of the support section 70. Specifically, a part of the luminous flux L1 is applied to the measurement target object S1 from a gap (opening) between the illumination restriction portion 702 and the illumination restriction portion 702.

According to the above-described second embodiment of the present invention, it is possible to keep stray light incident from the outside to a minimum and further enhance the strength of the distal end portion 33 of the measurement probe 7 while promoting a reduction in the diameter.

In the second embodiment of the present invention, the support section 70 may be formed using metal, resin, or the like that has flexibility and elasticity. Consequently, the measurement probe 7 is pressed against a treatment instrument channel of an endoscope when being inserted into the treatment instrument channel. Accordingly, the outer diameter of the support section 70 reduces to a size proportional to the inner diameter of the treatment instrument channel, and hence the measurement probe 7 can be easily inserted. Furthermore, it is possible to prevent the inside of the treatment instrument channel of the endoscope from being damaged.

First Modification of Second Embodiment

Figure 9:
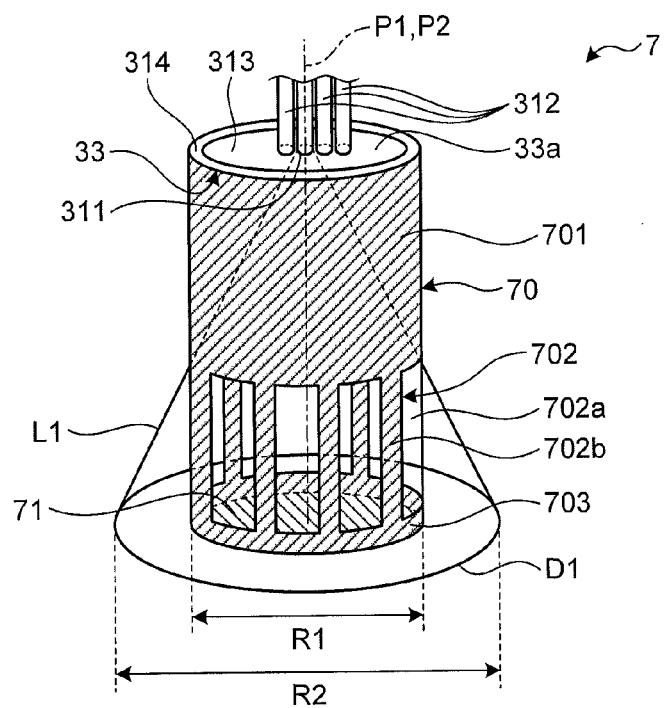
FIG. 9 is a perspective view schematically illustrating a distal end portion of a measurement probe including a support section according to a first modification of the second embodiment of the present invention.

In the second embodiment of the present invention, a light transmissive flat plate portion having a flat pate shape may be provided inside the annular portion 703. FIG. 9 is a perspective view schematically illustrating a distal end portion including a support section according to a first modification of the second embodiment of the present invention.

As illustrated in FIG. 9, in the measurement probe 7, the support section 70 may be provided with a flat plate-shaped flat plate portion 71 inside the annular portion 703. The flat plate portion 71 is formed using a transparent member such as glass material or plastic. Consequently, the flat plate portion 71 makes the surface of the measurement target object S1 flat.

According to the above-described first modification of the second embodiment of the present invention, the distance from the distal end surfaces of the illuminating fiber 311 and the light receiving fibers 312 and the measurement target object S1 can be kept constant. Accordingly, optical measurements can be made accurately.

Second Modification of Second Embodiment

Figure 10:
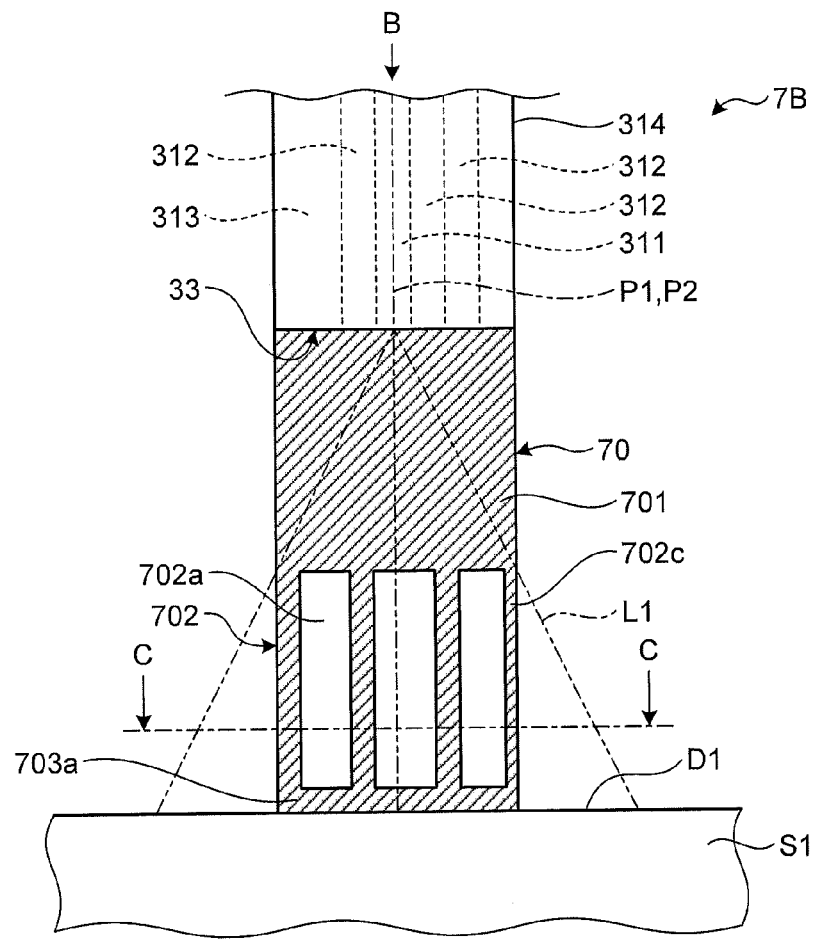
FIG. 10 is a side view of a distal end of a measurement probe including a support section according to a second modification of the second embodiment of the present invention.
Figure 11:
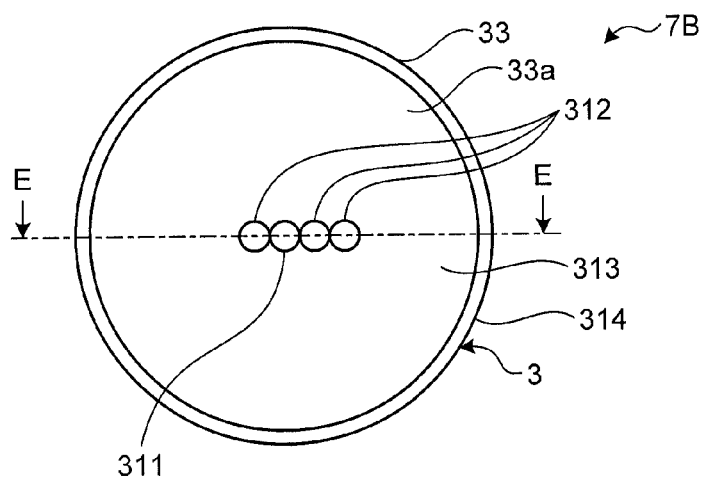
FIG. 11 is a front view of view B of FIG. 10.
Figure 12:
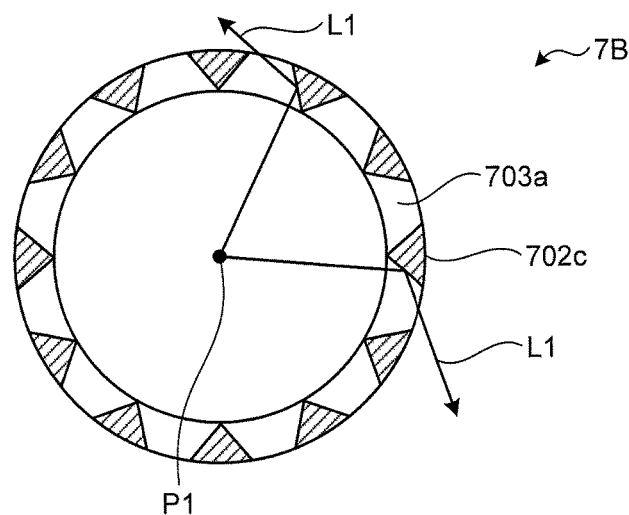
FIG. 12 is a cross-sectional view taken along line C-C of FIG. 10.
Figure 13:
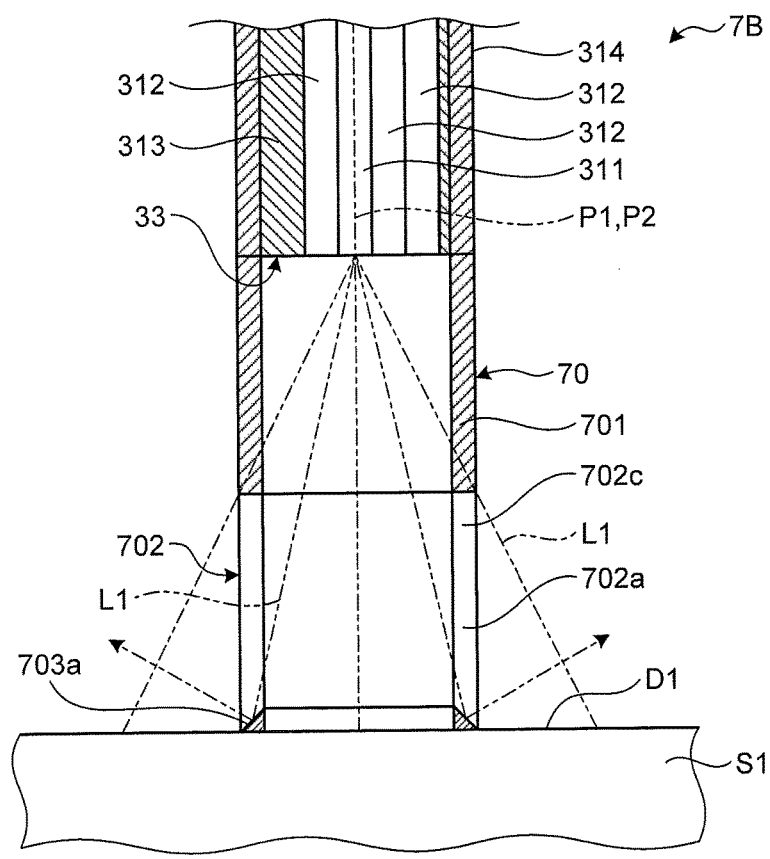
FIG. 13 is a cross-sectional view taken along line E-E of FIG. 11.

Moreover, in the second embodiment of the present invention, the shapes of the illumination restriction portion 702 and the annular portion 703 can be changed. FIG. 10 is a diagram illustrating a side view of a distal end of a measurement probe including a support section of a second modification of the second embodiment of the present invention. FIG. 11 is a front view of view B of FIG. 10. FIG. 12 is a cross-sectional view taken along line C-C of FIG. 10. FIG. 13 is a cross-sectional view taken along line E-E of FIG. 11.

As illustrated in FIGS. 10 to 13, when viewed from a cross section orthogonal to the longitudinal direction of a measurement probe 7B, the side portions 702c of the illumination restriction portion 702 are formed protruding toward the center of the measurement probe 7B. Moreover, an annular portion 703a is formed in such a manner as to slope toward the outer edge. In the measurement probe 7B constructed in this manner, it is possible to prevent the light receiving fibers 312 to receive the luminous flux L1 of the illumination light applied by the illuminating fiber 311 as external perturbations in the support section 70.

According to the above-described second modification of the second embodiment of the present invention, the side portions 702c and the annular portion 703a reflect external perturbations (noise) of the illumination light applied by the illuminating fiber 311 from light receiving areas of the light receiving fibers 312. Accordingly, optical measurements can be made more accurately.

Third Embodiment

Next, a third embodiment of the present invention is described. An optical measurement apparatus according to the third embodiment includes an air pump, and sends out air from the air pump to a measurement target object through a distal end of a measurement probe. The same reference numerals are assigned to parts having the same configurations as those of the optical measurement apparatuses and the measurement probes according to the above-mentioned first and second embodiments and their descriptions are omitted.

Figure 14:
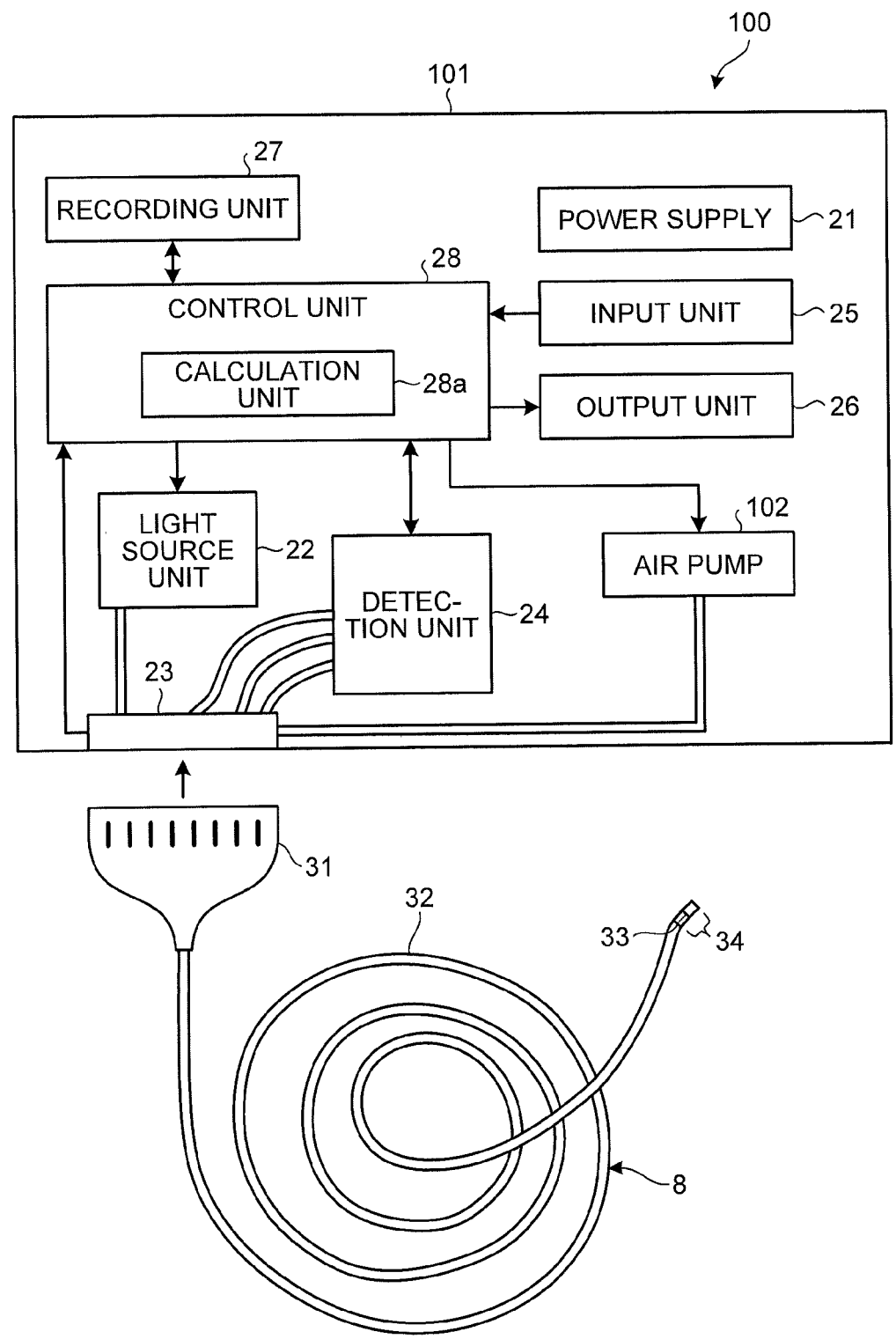
FIG. 14 is a block diagram schematically illustrating a configuration of an optical measurement apparatus according to a third embodiment of the present invention.

FIG. 14 is a block diagram schematically illustrating a configuration of the optical measurement apparatus according to the third embodiment of the present invention.

An optical measurement apparatus 100 illustrated in FIG. 14 includes a main body unit 101 and a measurement probe 8. The main body unit 101 includes the power supply 21, the light source unit 22, the connection unit 23, the detection unit 24, the input unit 25, the output unit 26, the recording unit 27, the control unit 28, and an air pump 102.

The air pump 102 sends out air toward the measurement target object S1 via the measurement probe 8 under the control of the control unit 28.

Figure 15:
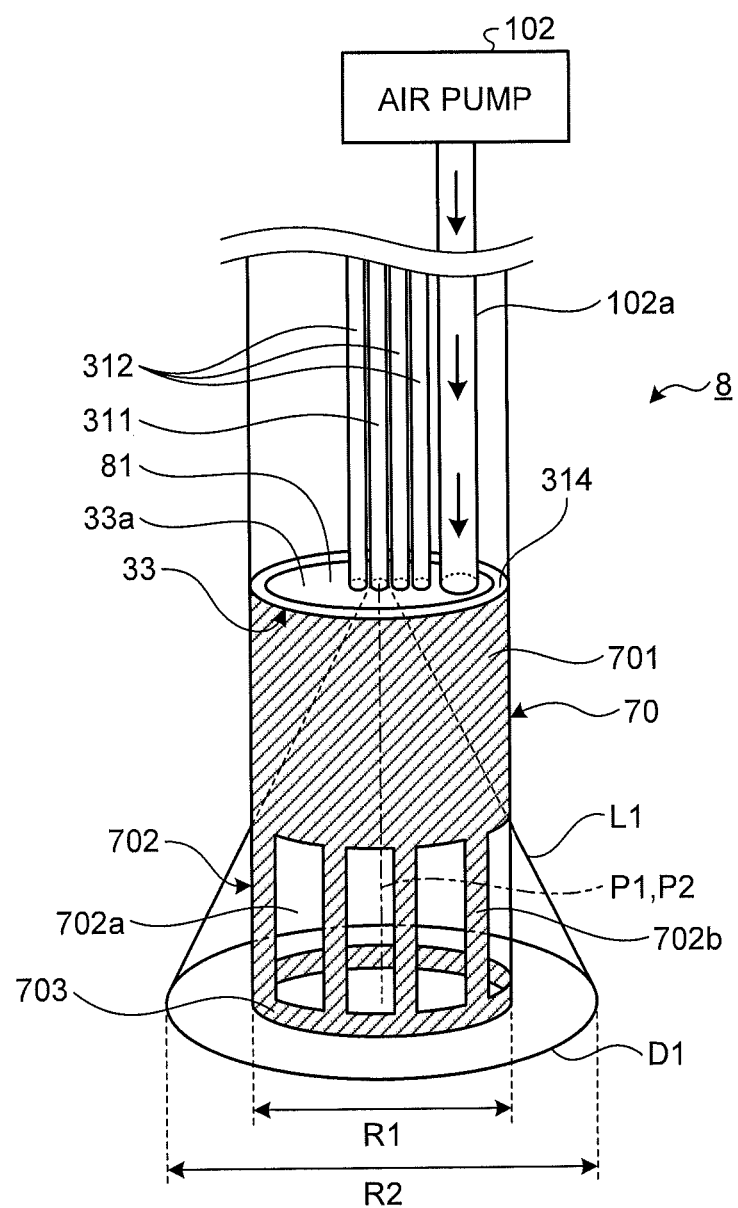
FIG. 15 is a perspective view schematically illustrating a distal end portion of a measurement probe including a support section according to the third embodiment of the present invention.

Next, the measurement probe 8 is described. FIG. 15 is a perspective view schematically illustrating a distal end portion of the measurement probe 8 including the support section 70.

The measurement probe 8 illustrated in FIG. 15 includes the illuminating fiber 311, the light receiving fibers 312, the coated section 314, an airline 102a, a holding section 81, and the support section 70.

Air is sent in the airline 102a from the air pump 102 of the main body unit 101. The air is blown from the end surface of the distal end toward the measurement target object S1.

The holding section 81 holds the distal ends of the illuminating fiber 311, the three light receiving fibers 312, and the airline 102a at the end surface 33a of the distal end portion 33 in the state where the distal ends neighbor one another in a straight line.

According to the above-described third embodiment of the present invention, the airline 102a blows air toward the measurement target object S1. Accordingly, foreign substances such as mucus and water on the surface of the measurement target object S1 can be removed at the time of measurement.

Fourth Embodiment

Next, a fourth embodiment of the present invention is described. An optical measurement apparatus according to the fourth embodiment includes an irrigation pump that sends out liquid and a suction pump that suctions the liquid. The optical measurement apparatus sends out liquid sent in from the irrigation pump from a distal end of a measurement probe and suctions the liquid from the distal end of the measurement probe. The same reference numerals are assigned to parts having the same configurations as those of the optical measurement apparatuses and the measurement probes according to the above-mentioned first and second embodiments and their descriptions are omitted.

Figure 16:
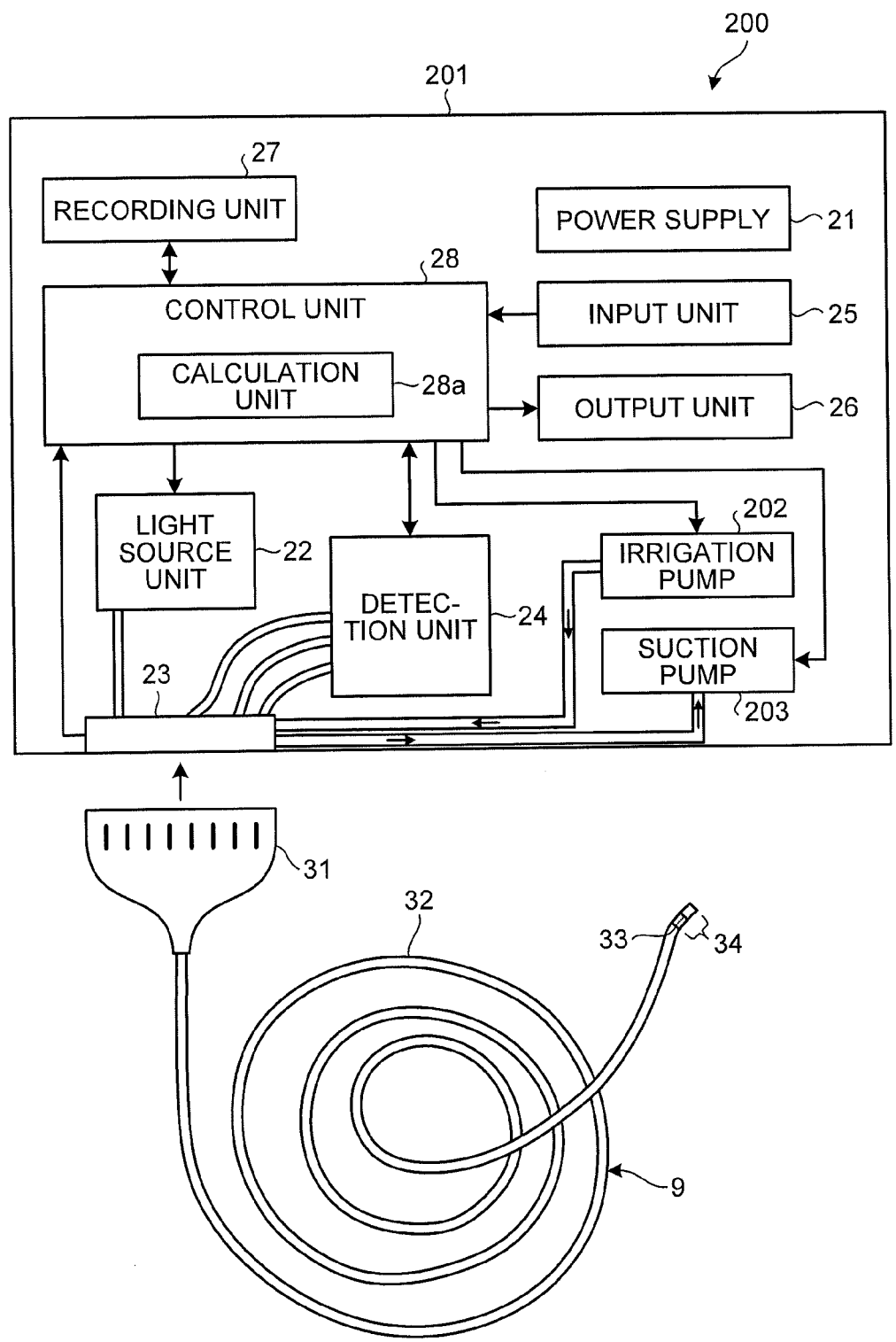
FIG. 16 is a block diagram schematically illustrating a configuration of an optical measurement apparatus according to a fourth embodiment of the present invention.

FIG. 16 is a block diagram schematically illustrating a configuration of the optical measurement apparatus according to the fourth embodiment of the present invention. As illustrated in FIG. 16, an optical measurement apparatus 200 includes a main body unit 201 and a measurement probe 9.

The main body unit 201 includes the power supply 21, the light source unit 22, the connection unit 23, the detection unit 24, the input unit 25, the output unit 26, the recording unit 27, the control unit 28, an irrigation pump 202, and a suction pump 203.

The irrigation pump 202 supplies liquid to the measurement probe 9 under the control of the control unit 28. The liquid here is water, saline solution, and the like.

The suction pump 203 suctions the liquid accumulated in a distal end portion of the measurement probe 9 under the control of the control unit 28.

Figure 17:
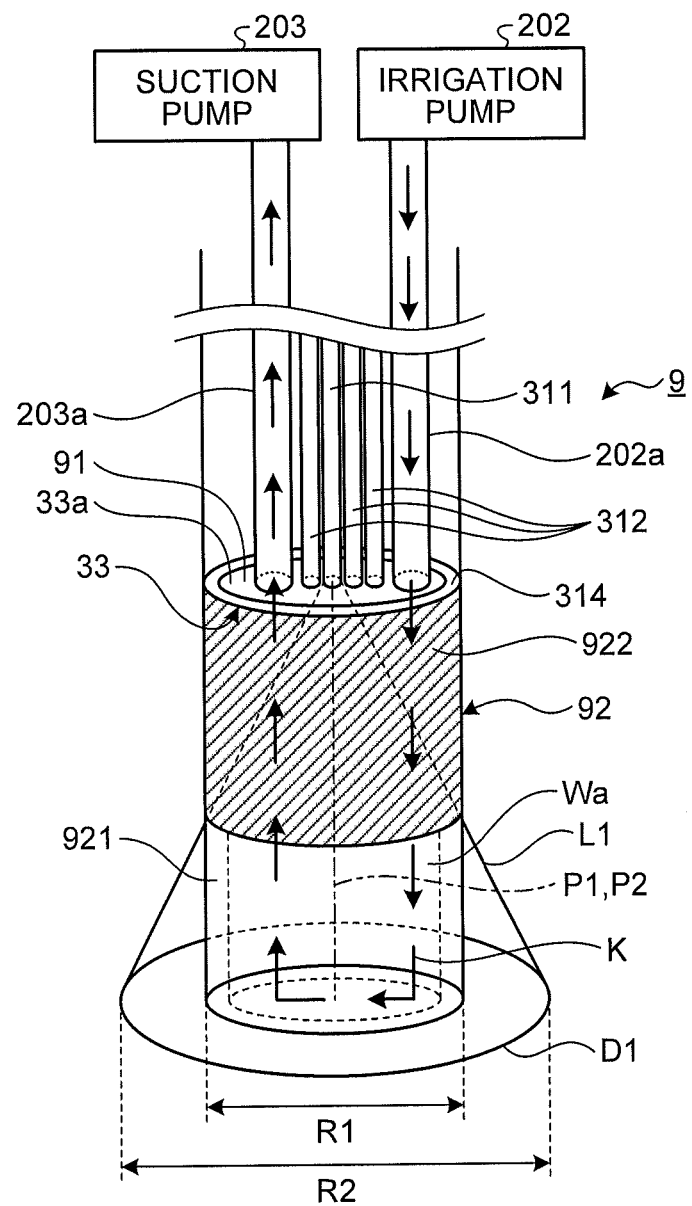
FIG. 17 is a perspective view schematically illustrating a distal end portion of a measurement probe including a support section according to the fourth embodiment of the present invention.

Next, the measurement probe 9 is described. FIG. 17 is a perspective view schematically illustrating the distal end portion of the measurement probe 9 including a support section.

The measurement probe 9 includes the illuminating fiber 311, the light receiving fibers 312, the coated section 314, an injection line 202a, a suction line 203a, a holding section 91, and a support section 92.

The injection line 202a supplies liquid sent from the irrigation pump 202 of the main body unit 201 to the support section 92 described below. The diameter of the injection line 202a is formed larger than the diameters of the illuminating fiber 311 and the light receiving fiber 312.

The suction line 203a suctions the liquid accumulated in the support section 92 described below. The suction line 203a is formed larger than the diameters of the illuminating fiber 311 and the light receiving fiber 312.

The holding section 91 holds the distal ends of the illuminating fiber 311, the three light receiving fibers 312, the injection line 202a, and the suction line 203a at the end surface 33a of the distal end portion 33 in the state where the distal ends are arranged in a straight line.

The support section 92 includes a tubular optical member 921 and a tubular reinforcement member 922 provided on an external marginal side of the optical member 921 to protect the optical member 921 from the external force.

The optical member 921 is attached to the end surface of the distal end portion 33, and makes the distance between the measurement target object S1 and the distal ends of the illuminating fiber 311 and the light receiving fibers 312 constant. The optical member 921 is constructed using glass material, plastic, or the like, and transmits the luminous flux L1 of the illumination light applied by the illuminating fiber 311.

The reinforcement member 922 is constructed using a member that is resistant to reflections such as metal or resin that shields the illumination light. The reinforcement member 922 prevents the optical member 921 from being bent or damaged by relieving the external force on the optical member 921. The reinforcement member 922 is formed in such a manner as to cover the side surface of the optical member 921 on the distal end side from the proximal end side. The reinforcement member 922 may be integrally formed with the optical member 921.

In the optical measurement apparatus 200 constructed in this manner, the irrigation pump 202 supplies liquid via the injection line 202a of the measurement probe 9 under the control of the control unit 28. In this case, liquid Wa is sent into an internal space K of the support section 92 created by the contact of the support section 92 with the measurement target object S1. The suction pump 203 subsequently suctions the liquid Wa from the internal space K via the suction line 203a. Consequently, the liquid Wa in the internal space K circulates. As a result, it is possible to make optical measurements with the internal space K filled with the liquid Wa while washing out the surface of the measurement target object S1.

According to the above-described fourth embodiment of the present invention, optical measurements can be made in a state where mucus, foreign substances, and the like on the surface of the measurement target object S1 have been removed.

According to the fourth embodiment of the present invention, the refractive index of liquid in the internal space K is adjusted. Consequently, in the case of LEBS, the optical characteristic as a spatial coherence length can be changed.

Other Embodiments

In the present invention, the support section may be detachable from the distal end portion of the measurement probe. Consequently, it is possible to make optical measurements in which the distance between a measurement target object and the distal end of the measurement probe has been set according to the measurement target object. In this case, in terms of the attachment/detachment of the support section, an external thread and an internal thread may be respectively provided to coupling portions (not illustrated) to enable the detachment. Naturally, a groove may be provided to one of them, and a claw to the other to enable the detachment.

In the present invention, light emitted by the light source unit is assumed to be visible to near-infrared light to acquire information mainly on a living tissue. However, light is not limited to visible light and near-infrared light for a living tissue and also for other applications.

Moreover, in the present invention, the wavelength range of the illumination light should be optimized to acquire information on a living tissue, and can be set freely according to the application. If spectral information is useful, it is possible to set a wavelength range to be slightly wide to cover the wavelength range of the spectral information, or set a plurality of bands discretely. If not required, it is possible to set a wavelength range by restricting the band to a certain degree.

Moreover, in the present invention, the end surfaces on the probe distal end side of the illuminating fiber and the light receiving fibers are arranged a predetermined distance away from the probe distal end in the substantially same plane. The position of the plane is called the distal end portion. The probe in the above-mentioned Patent Literature 1 is a probe that is optimized for coherent component measurement of backscattered light, called LEBS. In the case of the LEBS measurement of the present invention, the illuminating fiber and the light receiving fibers at the distal end portion are desired to be close to one another. Moreover, in the LEBS measurement of the present invention, relative intervals between the distal ends of the illuminating fiber and the light receiving fibers on the end surface are important. If a plurality of the intervals is set, or if a plurality of fibers having the same interval is set, the amount of signal information and SN of a signal increase, respectively. Accordingly, this configuration is desired for the application of LEBS. In the present invention, a description has been given focusing on the LEBS measurement. However, the present invention is not specialized in the measurement of a coherent component of backscattered light as in LEBS, but can also be applied to the measurement of diffusion light from a measurement target object, not limited to coherence, and imaging based on the diffusion light. The arrangement of the distal end portions of the illuminating fiber and the light receiving fibers at the end surface in this case does not need to be close, but may be a desired layout.

In this manner, the present invention may include various embodiments that are not described herein, and various design changes and the like can be made within the scope of the technical idea specified by the claims.

According to the above-described embodiments and their modifications of the present invention, measurements can be made with higher accuracy while a reduction in the diameter is promoted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A measurement probe configured to be detachably connected to an optical measurement apparatus for optically measuring a living tissue, the measurement probe comprising:
   an illuminating fiber configured to apply illumination light to the living tissue;
   a plurality of light receiving fibers configured to receive, at different positions, backscattering light that is applied by the illuminating fiber and that is backreflected and/or backscattered from the living tissue; and
   a support section that is substantially cylindrical and that is configured to make a distance from a distal end of the illuminating fiber and of the plurality of light receiving fibers to the living tissue constant,
      the support section permitting the illumination light to pass through at least a part of a side surface of the support section, and
      a distal end of the support section being configured to contact the living tissue while the measurement probe is in use,
   wherein an illumination area of the illumination light, applied by the illuminating fiber on the living tissue, is larger than an area of the distal end of the support section.

2. The measurement probe according to claim 1, wherein the support section includes:
   an optical member that is cylindrical and that is configured to (i) relay the illumination light applied by the illuminating fiber and (ii) apply the illumination light to the living tissue; and
   a reinforcement member that is in contact with a side wall of the optical member, the reinforcement member forming at least a part of the side wall of the optical member such that a length of the reinforcement member in a longitudinal direction of the measurement probe is smaller than a length of the optical member in the longitudinal direction, and the reinforcement member including a material that absorbs the illumination light.

3. The measurement probe according to claim 1, wherein a central axis of the illuminating fiber is coplanar with a central axis of the measurement probe.

4. The measurement probe according to claim 1, wherein a central axis of the illuminating fiber is off-set with regard to a central axis of the measurement probe.

5. The measurement probe according to claim 2, wherein the optical member has a tubular shape.

6. The measurement probe according to claim 5, further comprising:
   an injection line configured to inject liquid supplied from outside the measurement probe into an internal space of the optical member; and
   a suction line configured to suction at least the liquid from the internal space of the optical member,
   wherein the injected liquid fills an inside of the support section and functions as a part of the optical member.

7. The measurement probe according to claim 1, wherein the support section includes:
   a tube portion that is in a hollow tubular-shape and that has a substantially cylindrical shape with the same diameter as an outer diameter of the measurement probe, the tube portion including a member that absorbs the illumination light, the tube portion being configured not to shield the illumination light;
   an illumination restriction portion that is configured to shield the illumination light; and
   a window portion that is provided in the illumination restriction portion to permit the passage of at least part of the illumination light.

8. The measurement probe according to claim 7, wherein the support section further includes a flat plate portion configured to transmit light, at a part of the distal end of the support section.

9. The measurement probe according to claim 7, wherein the illumination restriction portion includes a plurality of side portions protruding toward the center of the measurement probe, as viewed from a cross section orthogonal to a longitudinal direction of the measurement probe.

10. The measurement probe according to claim 5, further comprising an airline configured to send air from outside the measurement probe.

11. The measurement probe according to claim 1, wherein the distal end of the support section inclines with respect to a longitudinal direction of the measurement probe.

12. The measurement probe according to claim 1, wherein the support section is detachable from a distal end portion of the measurement probe.

13. The measurement probe according to claim 1, wherein:
   the measurement probe is configured to be introduced into an inside of a subject through an instrument channel to measure the living tissue, and
   the illumination area is larger than an outer diameter of the measurement probe that passes through the instrument channel.

* * * * *